(12) United States Patent
Hsung et al.

(10) Patent No.: US 10,420,946 B2
(45) Date of Patent: Sep. 24, 2019

(54) MEDICAL DEVICE FOR TREATING CARDIAC ARRHYTHMIA

(71) Applicant: SHANGHAI MICROPORT MEDICAL (GROUP) CO., LTD., Shanghai (CN)

(72) Inventors: Jean Cheui Hsung, Shanghai (CN); Guiling Li, Shanghai (CN); Min Huang, Shanghai (CN); Xinxin Chen, Shanghai (CN)

(73) Assignee: SHANGHAI MICROPORT MEDICAL (GROUP) CO., LTD., Shanghai (CN)

(*) Notice: Subject to any disclaimer, the term of this patent is extended or adjusted under 35 U.S.C. 154(b) by 51 days.

(21) Appl. No.: 15/550,634

(22) PCT Filed: Jan. 8, 2016

(86) PCT No.: PCT/CN2016/070510
§ 371 (c)(1),
(2) Date: Aug. 11, 2017

(87) PCT Pub. No.: WO2016/131349
PCT Pub. Date: Aug. 25, 2016

(65) Prior Publication Data
US 2018/0036541 A1   Feb. 8, 2018

(30) Foreign Application Priority Data

Feb. 17, 2015 (CN) .......................... 2015 1 0086552

(51) Int. Cl.
*A61N 1/365* (2006.01)
*A61N 1/39* (2006.01)
(Continued)

(52) U.S. Cl.
CPC ......... *A61N 1/36514* (2013.01); *A61N 1/025* (2013.01); *A61N 1/056* (2013.01);
(Continued)

(58) Field of Classification Search
CPC .... A61N 1/3684; A61N 1/3682; A61N 1/371; A61N 1/3688; A61N 1/3706;
(Continued)

(56) References Cited

U.S. PATENT DOCUMENTS 5,273,035 A    12/1993   Markowitz et al.
5,716,384 A    2/1998    Snell
(Continued)

FOREIGN PATENT DOCUMENTS

CN    101500645 A    8/2009
CN    102300603 A    12/2011
(Continued)

*Primary Examiner* — Deborah L Malamud
(74) *Attorney, Agent, or Firm* — Muncy, Geissler, Olds & Lowe, P.C.

(57) ABSTRACT

A medical device for treating cardiac arrhythmia includes a microprocessor. A MCU configures the medical device to operate in a modified DVI (R) mode in which: when receiving a signal indicating the sensing of an atrial event, the MCU sets a PANP interval and sends to a time control unit a signal; if a scheduled post-ventricular atrial escaping interval is to end at a time not within the PANP internal, the MCU sends respective signals to a pacing control/generation unit and the time control unit to dictate the pacing control/generation unit and control a second timing unit to use a PAVI as a next ventricular escape interval; and if the scheduled post-ventricular atrial escaping interval is to end within the PANP interval, the MCU sends a signal to the time control unit, controlling the second timing unit to use the PAVI as the next ventricular escape interval.

10 Claims, 3 Drawing Sheets

(51) Int. Cl.
*A61N 1/362* (2006.01)
*A61N 1/05* (2006.01)
*A61N 1/368* (2006.01)
*A61N 1/02* (2006.01)

(52) U.S. Cl.
CPC .......... *A61N 1/362* (2013.01); *A61N 1/3622* (2013.01); *A61N 1/3682* (2013.01); *A61N 1/3684* (2013.01); *A61N 1/39* (2013.01)

(58) Field of Classification Search
CPC .... A61N 1/3712; A61N 1/362; A61N 1/3714; A61N 1/36; A61N 1/37; A61N 1/025; A61N 1/36843; A61N 1/37512; A61B 5/0464; A61B 5/6869; A61B 5/4836; A61B 5/046; A61B 5/0006; A61B 5/0402; A61B 5/0245; G06F 19/3456
See application file for complete search history.

(56) References Cited

U.S. PATENT DOCUMENTS

| | | |
|---|---|---|
| 5,749,906 A | 5/1998 | Kieval et al. |
| 2003/0036777 A1 | 2/2003 | Sheth et al. |
| 2007/0027488 A1 | 2/2007 | Kaiser et al. |
| 2007/0191891 A1 | 8/2007 | Burnes et al. |
| 2007/0293898 A1 | 12/2007 | Sheldon et al. |
| 2013/0197599 A1* | 8/2013 | Sambelashvili ....... A61N 1/368 607/25 |

FOREIGN PATENT DOCUMENTS

| | | |
|---|---|---|
| CN | 104623804 A | 5/2015 |
| CN | 104623805 A | 5/2015 |
| CN | 104623809 A | 5/2015 |

\* cited by examiner

MEDICAL DEVICE FOR TREATING CARDIAC ARRHYTHMIA

TECHNICAL FIELD

The present invention relates to the field of medical devices and, in particular, to a medical device for treating cardiac arrhythmia.

BACKGROUND

A cardiac pacemaker is an electronic therapeutic instrument that is implanted in the body and employs a battery-powered pulse generator to deliver electrical pulses. The pulses are transferred via a lead to an electrode to stimulate the heart muscle to which the electrode is attached, resulting in the heart activation and contraction, achieving the treatment of heart dysfunction caused by some cardiac arrhythmia conditions.

A DDD pacemaker is able to sense and pace the atria and ventricles. However, improper pacing may cause some undesirable events.

An atrial pacing pulse delivered during the atrial vulnerable period may induce atrial tachycardia or other kinds of arrhythmia. This often takes place in the following two circumstances:

1. In a dual-chamber tracking mode such as DDD, it usually happens close to an atrial-sensed event within an atrial refractory period and is conventionally prevented by introduction of non-competitive atrial pacing (NCAP). In the DDD or DDDR mode, if this function is enabled, an atrial-sensed event within a refractory period will initialize an NCAP interval. If a scheduled atrial pacing event is to occur within the NCAP interval, then the scheduled atrial pacing event is delayed until the end of the NCAP interval. The delay in atrial pacing will impact the timing of ventricular events. Therefore, In order to maintain a stable ventricular heart rate, the paced atrioventricular (PAV) interval needs to be shortened.

However, with the conventional implementation, there is likelihood for an over-shortened PAV, a relatively great lower frequency limit, as well as a ventricular frequency lower than the lower frequency limit in case of a long atrial refractory period after ventricular pacing.

2. In a DVI or DVIR mode of conventional dual-chamber pacemakers, due to the absence of effective atrial sensing, the aforementioned issue may occur close to an atrial event within or not within an atrial refractory period and leads to severe tachycardia. Therefore, there is a need in the art for a novel medical device for treating cardiac arrhythmia, which can solve the problem of induced atrial tachycardia.

SUMMARY OF THE INVENTION

It is an objective of the present invention to address the issue of induced severe atrial tachycardia arising from the use of the existing DVI medical devices by presenting a medical device for treating cardiac arrhythmia.

To this end, the present invention provides a medical device for treating cardiac arrhythmia, including a microprocessor and a digital/analog module in connection with the microprocessor, the microprocessor including a main control unit and a time control unit, the digital/analog module including a pacing control/generation unit and a sense control/amplification unit, the time control unit at least including a first timing unit and a second timing unit, wherein The main control unit is configured to cause the medical device to operate in a modified DVI (R) mode in which:

when receiving a signal indicating sensing of an atrial event by the sense control/amplification unit, the main control unit sets a post-atrial non-pacing interval and sends a signal to the time control unit, controlling the first timing unit to operate in a timing mode for a duration equal to a duration of the post-atrial non-pacing interval; if a scheduled post-ventricular atrial escaping interval (PVAEI) is expected to end at a time not within the post-atrial non-pacing interval, the main control unit sends respective signals to the sense control/amplification unit and the time control unit to dictate the pacing control/generation unit to deliver a pacing pulse and to control the second timing unit to use a paced atrioventricular interval as a next ventricular escape interval; and if the scheduled post-ventricular atrial escaping interval is to end within the post-atrial non-pacing interval, the main control unit sends a signal to the time control unit such that the second timing unit is controlled to use the paced atrioventricular interval as the next ventricular escape interval.

Additionally, in the medical device for treating cardiac arrhythmia, upon receiving the signal indicating sensing of an atrial event by the sense control/amplification unit, the main control unit may acquire information about whether a post-atrial non-pacing function is activated, and if the post-atrial non-pacing function is activated, sets a post-atrial non-pacing interval and sends a signal to the time control unit such that the first timing unit is controlled to operate in a timing mode for a duration equal to a duration of the post-atrial non-pacing interval.

Additionally, in the medical device for treating cardiac arrhythmia, upon receiving another signal indicating sensing of another atrial event by the sense control/amplification unit within the post-atrial non-pacing interval, the main control unit may send a signal to the time control unit such that the first timing unit is controlled to restart timing for another duration equal to a duration of the post-atrial non-pacing interval.

Additionally, in the medical device for treating cardiac arrhythmia, the post-atrial non-pacing interval may start at a time when the atrial event is sensed.

Additionally, in the medical device for treating cardiac arrhythmia, concurrently with setting of the post-atrial non-pacing interval, the main control unit may set up a post-atrial non-pacing interval type marker.

Additionally, in the medical device for treating cardiac arrhythmia, at an end of the post-atrial non-pacing interval, the main control unit may clear the post-atrial non-pacing interval type marker.

Additionally, in the medical device for treating cardiac arrhythmia, set of the post-atrial non-pacing interval type marker may indicate a time within the post-atrial non-pacing interval, while clearing of the post-atrial non-pacing interval type marker may indicate a time not within the post-atrial non-pacing interval.

Additionally, in the medical device for treating cardiac arrhythmia, if the scheduled post-ventricular atrial escaping interval is to end at a time within the post-atrial non-pacing interval, the main control unit may mark a virtual atrial pacing event and prohibits a scheduled atrial pacing pulse, and if the scheduled post-ventricular atrial escaping interval is to end at a time not within the post-atrial non-pacing interval, the main control unit may mark a real atrial pacing event and sends a signal to dictate the pacing control/generation unit to deliver an atrial pacing pulse.

Additionally, in the medical device for treating cardiac arrhythmia, when a virtual atrial pacing event is marked, the main control unit may set the next ventricular escape interval with the time when the virtual atrial pacing event is marked as a start point.

Additionally, in the medical device for treating cardiac arrhythmia, when a real atrial pacing event is marked, the main control unit may set the next ventricular escape interval with the time when the real atrial pacing event is marked as a start point.

The medical device for treating cardiac arrhythmia according to the present invention offers the following benefits: since upon sensing an atrial event by the digital/analog module, the microprocessor is notified and sets a PANP interval, the issue of inducing atrial tachycardia is addressed and the medical device can be suitably used with defibrillators and pacemakers.

DETAILED DESCRIPTION

The medical device for treating cardiac arrhythmia according to the present invention will be described in greater detail below with reference to the accompanying drawings as well as to particular embodiments. The features and advantages of the invention will be more apparent from the following detailed description, as well as from the appended claims. It is noted that the accompanying drawings are provided in a very simplified form not necessarily presented to scale, with the only purpose of facilitating convenience and clarity in explaining the embodiments.

Figure 1:
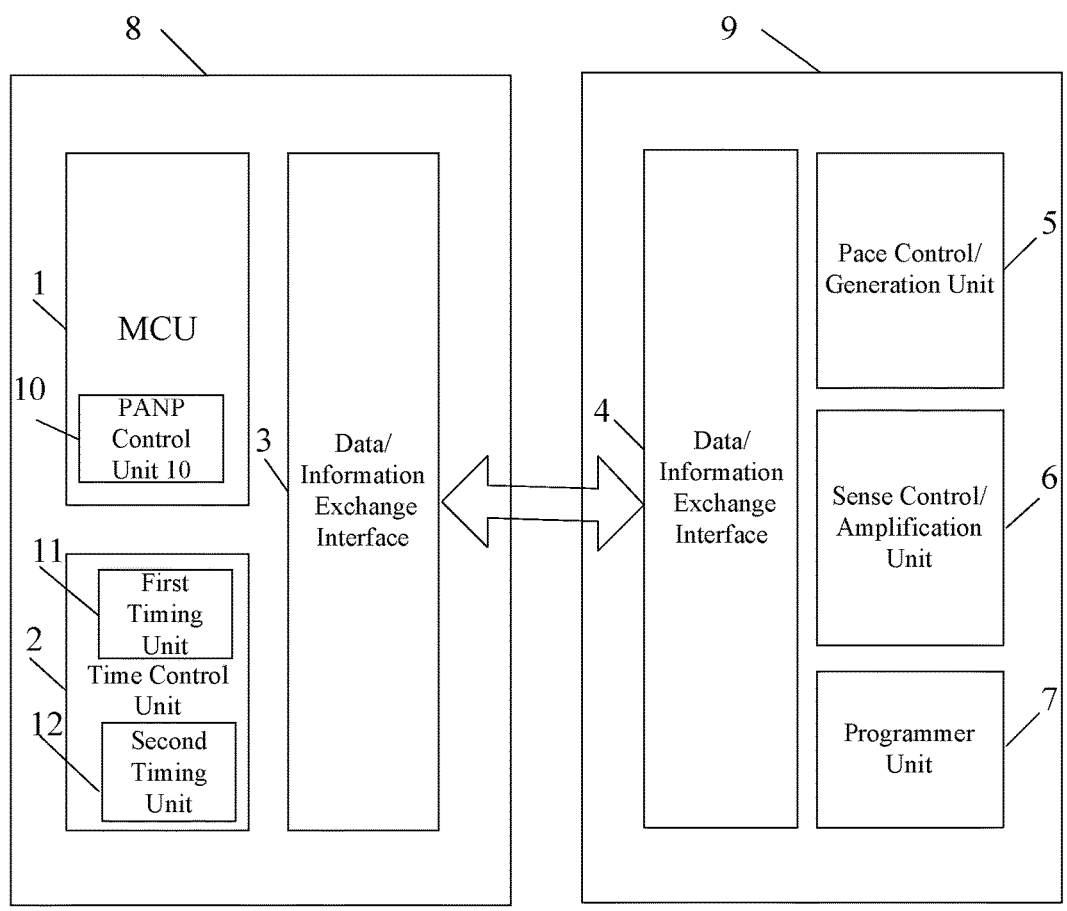
FIG. 1 is a structural schematic of a medical device for treating cardiac arrhythmia according to a preferred embodiment of the present invention.

FIG. 1 is a structural schematic of a medical device for treating cardiac arrhythmia according to a preferred embodiment of the present invention, to which the present invention can be effectively applied. The figure is intended to be considered as an example of the device embodying the present invention rather than a limitation to the invention.

As shown in FIG. 1, the medical device for treating cardiac arrhythmia of the present invention includes a microprocessor 8 and a digital/analog module 9 in connection with the microprocessor. Selection and implementation of the microprocessor 8 is not particularly limited. The digital/analog module 9 is required to be able to sense an external signal, deliver externally acting signal and carry out external data exchanges.

Further, the microprocessor 8 includes a main control unit (MCU) 1, a time control unit 2 and a data/information exchange interface 3. The time control unit 2 at least includes a first timing unit 11 and a second timing unit 12. The MCU 1 allows for receiving and processing of a message from the digital/analog module 9 about the occurrence of an event and for control of an event needed to occur and the like. The MCU 1 may selectively render the time control unit 2 able to provide time-related control functions such as timing and timekeeping. For example, the time control unit 2 may be made capable of capturing and recording the time of occurrence of an event and controlling the exact time at which an event needed to occur. As an example, upon receipt of an atrial event signal, the MCU 1 may set a post-atrial non-pacing (PANP) interval and send a signal to the time control unit 2. The first timing unit 11 may be caused to operate as a timer for a duration equal to that of the PANP interval. As another example, the second timing unit 12 that functions as a timer for a duration equal to that of a paced atrioventricular interval (PAVI) serving as the next ventricular escape interval may provide an exact time for the occurrence of the ventricular pacing event. The data/information exchange interface 3 may exchange data or information with other modules in the device. The data/information exchange interface 3 may either be a conventional I/O interface or a serial or parallel data transmission module. In the present embodiment, the data/information exchange interface 3 is able to receive information about a sensed event, deliver a request for a pacing event, perform serial data interactions and clock data interactions, etc. In addition, the inventive device may include other units. For example, the MCU 1 may further include a unit 10 capable of controlling the PANP interval (hereinafter referred to as the "PANP control unit 10"). Upon reception of an atrial event signal, the MCU 1 may obtain a signal indicating whether the PANP control unit 10 is activated or not. If the PANP control unit 10 is activated, then the MCU 1 sets a PANP interval and sends a signal to the time control unit 2 so that the first timing unit 11 is caused to enter the mode in which it acts as a timer for a duration equal to that of the PANP interval.

Additionally, the digital/analog module 9 may further include another data/information exchange interface 4, a pacing control/generation unit 5, a sense control/amplification unit 6 and a programmer unit 7. The data/information exchange interface 4 can interact with the data/information exchange interface 3. It is a matter of course that the two data/information exchange interfaces can assume the same form or different forms. The pacing control/generation unit 5 can receive a pacing request from the microprocessor 8, generate an externally acting signal with a required strength and undertake some control tasks. The strength, type and the like of the signal vary depending on the object on which it acts. The sense control/amplification unit 6 is capable of capturing, recognizing, notifying the microprocessor 8 of, and amplifying an external signal such as, for example, a heart signal. The programmer unit 7 can exchange information with an external entity such as, for example, a user.

Figure 2:
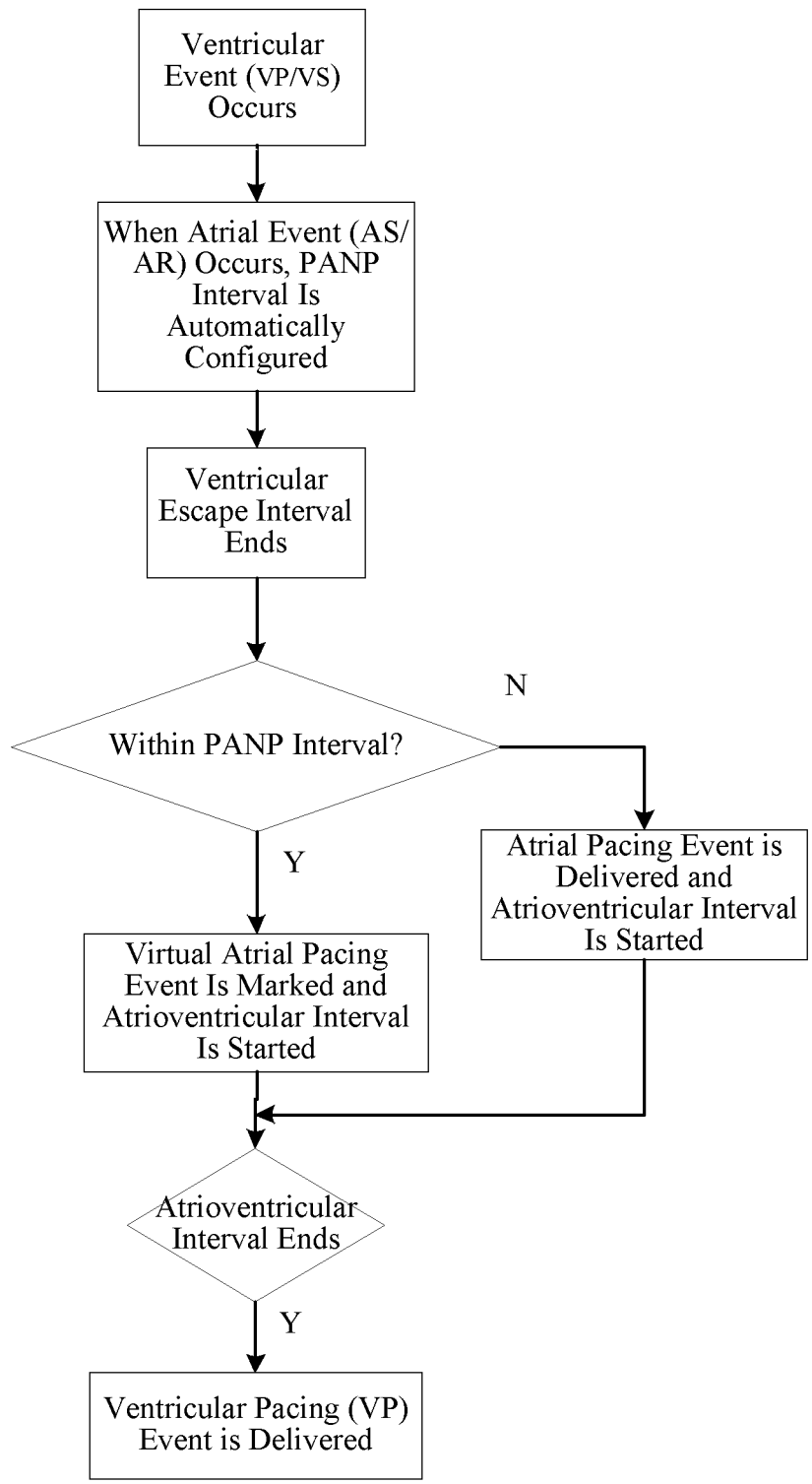
FIG. 2 is a flowchart illustrating operations performed by a medical device for treating cardiac arrhythmia according to a preferred embodiment of the present invention.

As shown in FIG. 2, the MCU 1 of the microprocessor can cause the medical device to operate in a modified DVI (R) mode and provide the ability to sense an atrial event. Once the sense control/amplification unit 6 in the digital/analog module has sensed an atrial event, it immediately sends a signal to the MCU 1. After receiving the signal, the MCU 1 obtains, from the PANP control unit 10, information about whether the PANP function is activated or not. If the PANP (post-atrial non-pacing) function of the PANP control unit 10 is currently activated, then the MCU 1 immediately sets a PANP interval. Otherwise, the MCU 1 may do nothing. If a scheduled post-ventricular atrial escaping interval (PVAEI) is to occur within the PANP interval, the MCU 1 may control the pacing control/generation unit 5 such that a scheduled atrial pacing is not performed. That is, instead of sending a signal dictating the pacing control/generation unit 5 to deliver an atrial pacing pulse, the MCU 1 sends a signal to the time control unit 2, under the control of which the second timing unit 12 uses the PAVI to set the next ventricular escape interval. If scheduled post-ventricular atrial escaping interval is to occur at a time not within the PANP, an atrial pacing pulse will be delivered as scheduled. That is, the MCU 1 sends respective signals to the pacing control/generation unit 5 and the time control unit 2 so as to cause the pacing control/generation unit 5 to deliver the atrial pacing pulse and cause the second timing unit 12 to use the PAVI to set the next ventricular escape interval. In the event of receiving a signal indicating that the sense control/amplification unit 5 has sensed another atrial event within the PANP interval, the MCU 1 may send a signal to the time control unit 2 so as to control the first timing unit 11 to restart timing for another duration equal to that of the PANP interval.

Figure 3:
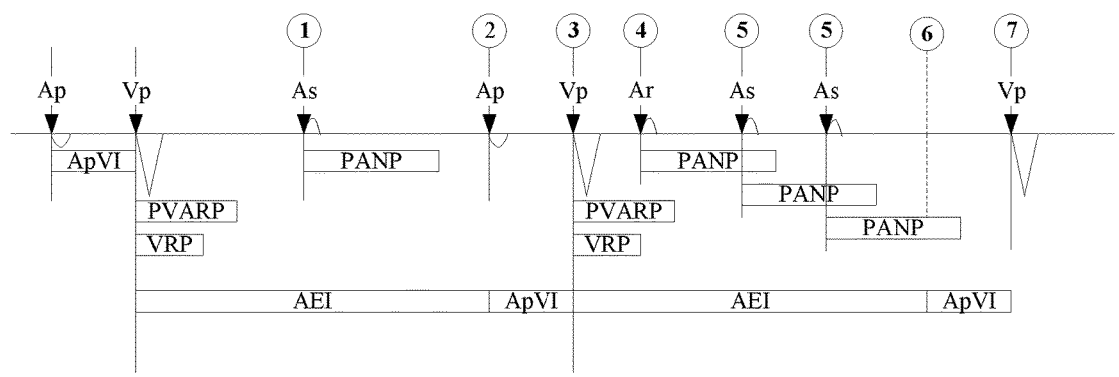
FIG. 3 is a diagram showing a temporal sequence of actions taken by a medical device for treating cardiac arrhythmia according to a preferred embodiment of the present invention.

Reference is further made to FIG. 3, a diagram showing a temporal sequence of actions taken by a medical device for treating cardiac arrhythmia according to the present invention.

At time instant ①, after receiving a signal indicating that an atrial event has been sensed, the MCU 1 initiates a PANP interval and marks it with a PANP interval type identifier. It is particularly noted that, no matter whether the event is sensed within or not within a post-ventricular atrial refractory period (PVARP), the PANP interval will be initiated.

According to the present invention, the modified DVI (R) mode is a dual-chamber mode allowing both A (atrial) and V (ventricular) pacing and sensing of both A and V signals. However, for A sensing, the medical device is so designed that the digital/analog module can only sense an atrial signal (AS) and notify the MCU about it, without enabling the MCU to track the V pacing based on the AS. Thus, the medical device is of an inhibited type.

Further, an A pacing stimulus is delivered prior to a V pacing stimulus, and the atrioventricular interval (AVI) satisfies the PAVI.

At time instant ②, when in the modified DVI (R) mode, after receiving a VS or VP signal, the MCU 1 calculates a post-ventricular atrial escape interval (AEI) as AEI=Effective Lower Frequency Limit (eff_lrl)–Effective Atrioventricular Escape Interval (eff_AVI). Wherein, in case of the VS signal, it is necessary for eff_AEI to further take account in the reminder of the atrioventricular interval (effective pavi–AV_interval).

At time instant ③, a ventricular pacing pulse is delivered at the end of the paced atrioventricular interval (PAVI), and the PVARP, VRP (Ventricular Refractory Period) and AEI are restarted.

At time instant ④, when receiving a signal of an atrial-sensed event, the MCU 1 initiates a PANP interval, and the first timing unit 11 starts to operate in a timing mode for a duration equal to that of the PANP interval. In this case, the event is sensed within the PVARP.

At time instant ⑤, when receiving a signal of an atrial-sensed event, the MCU 1 initiates a PANP interval, and the first timing unit 11 starts to operate in a timing mode for a duration equal to that of the PANP interval. In this case, the event is sensed at a time not within the PVARP.

At time instant ⑥, when the post-ventricular AEI is to end at a time within the PANP interval, the pacing control/generation unit 5 does not deliver the scheduled atrial pacing pulse. Instead, the scheduled delivery time for the pulse that has not been eventually delivered is used in the calculation of the next ventricular pacing time which serves as a timer duration for the second timing unit 12. In other words, the post-atrial ventricular escape interval is taken as the escape interval. Further, the PANP interval type identifier is cleared by the MCU 1.

At time instant ⑦, when the post-ventricular AEI is to end at a time not within the PANP interval, the MCU 1 may send a signal to indicate the pacing control/generation unit 5 to deliver an atrial pacing pulse and take the PAVI as the escape interval. In addition, the MCU 1 may send a signal to the time control unit 2 to take the PAVI as a timer duration. In this way, synchronized atrioventricular pacing and hence improved hemodynamics can be achieved.

The foregoing description presents merely a few preferred embodiments of the present invention and does not limit the scope thereof in any sense. All changes or modifications made in light of the above disclosure by any person of ordinary skill in the art fall within the scope of protection set forth in the appended claims.

What is claimed is:

1. A medical device for treating cardiac arrhythmia, comprising a microprocessor and a digital/analog module in connection with the microprocessor, the microprocessor comprising a main control unit and a time control unit, the digital/analog module comprising a pacing control/generation unit and a sense control/amplification unit, the time control unit at least comprising a first timing unit and a second timing unit, wherein
the main control unit is configured to cause the medical device to operate in a modified DVI (R) mode in which:
when receiving a signal indicating sensing of an atrial event by the sense control/amplification unit, the main control unit sets a post-atrial non-pacing interval and sends a signal to the time control unit, controlling the first timing unit to operate in a timing mode for a duration equal to a duration of the post-atrial non-pacing interval; if a scheduled post-ventricular atrial escaping interval is expected to end at a time not within the post-atrial non-pacing interval, the main control unit sends respective signals to the sense control/amplification unit and the time control unit to dictate the pacing control/generation unit to deliver an atrial pacing pulse and to control the second timing unit to use a paced atrioventricular interval as a next ventricular escape interval; and if the scheduled post-ventricular atrial escaping interval is to end within the post-atrial non-pacing interval, the pacing control/generation unit does not deliver an atrial pacing pulse, and the main control unit sends a signal to the time control unit such that the second timing unit is controlled to use the paced atrioventricular interval as the next ventricular escape interval.

2. The medical device for treating cardiac arrhythmia according to claim 1, wherein upon receiving the signal indicating sensing of an atrial event by the sense control/amplification unit, the main control unit acquires information about whether a post-atrial non-pacing function is activated, and if the post-atrial non-pacing function is activated, sets a post-atrial non-pacing interval and sends a signal to the time control unit such that the first timing unit is controlled to operate in a timing mode for a duration equal to a duration of the post-atrial non-pacing interval.

3. The medical device for treating cardiac arrhythmia according to claim 1, wherein upon receiving another signal indicating sensing of another atrial event by the sense control/amplification unit within the post-atrial non-pacing interval, the main control unit sends a signal to the time control unit such that the first timing unit is controlled to restart timing for another duration equal to a duration of the post-atrial non-pacing interval.

4. The medical device for treating cardiac arrhythmia according to claim 1, wherein the post-atrial non-pacing interval starts at a time when the atrial event is sensed.

5. The medical device for treating cardiac arrhythmia according to claim 1, wherein concurrently with setting of the post-atrial non-pacing interval, the main control unit sets up a post-atrial non-pacing interval type marker.

6. The medical device for treating cardiac arrhythmia according to claim 5, wherein at an end of the post-atrial non-pacing interval, the main control unit clears the post-atrial non-pacing interval type marker.

7. The medical device for treating cardiac arrhythmia according to claim 5, wherein set of the post-atrial non-pacing interval type marker indicates a time within the post-atrial non-pacing interval, while clearing of the post-atrial non-pacing interval type marker indicates a time not within the post-atrial non-pacing interval.

8. The medical device for treating cardiac arrhythmia according to claim 1, wherein if the scheduled post-ventricular atrial escaping interval is to end at a time within the post-atrial non-pacing interval, the main control unit marks a virtual atrial pacing event and prohibits a scheduled atrial pacing pulse, and if the scheduled post-ventricular atrial escaping interval is to end at a time not within the post-atrial non-pacing interval, the main control unit marks a real atrial pacing event and sends a signal to dictate the pacing control/generation unit to deliver an atrial pacing pulse.

9. The medical device for treating cardiac arrhythmia according to claim 8, wherein when a virtual atrial pacing event is marked, the main control unit sets the next ventricular escape interval with the time when the virtual atrial pacing event is marked as a start point.

10. The medical device for treating cardiac arrhythmia according to claim 8, wherein when a real atrial pacing event is marked, the main control unit sets the next ventricular escape interval with the time when the real atrial pacing event is marked as a start point.

* * * * *